Figure 1:
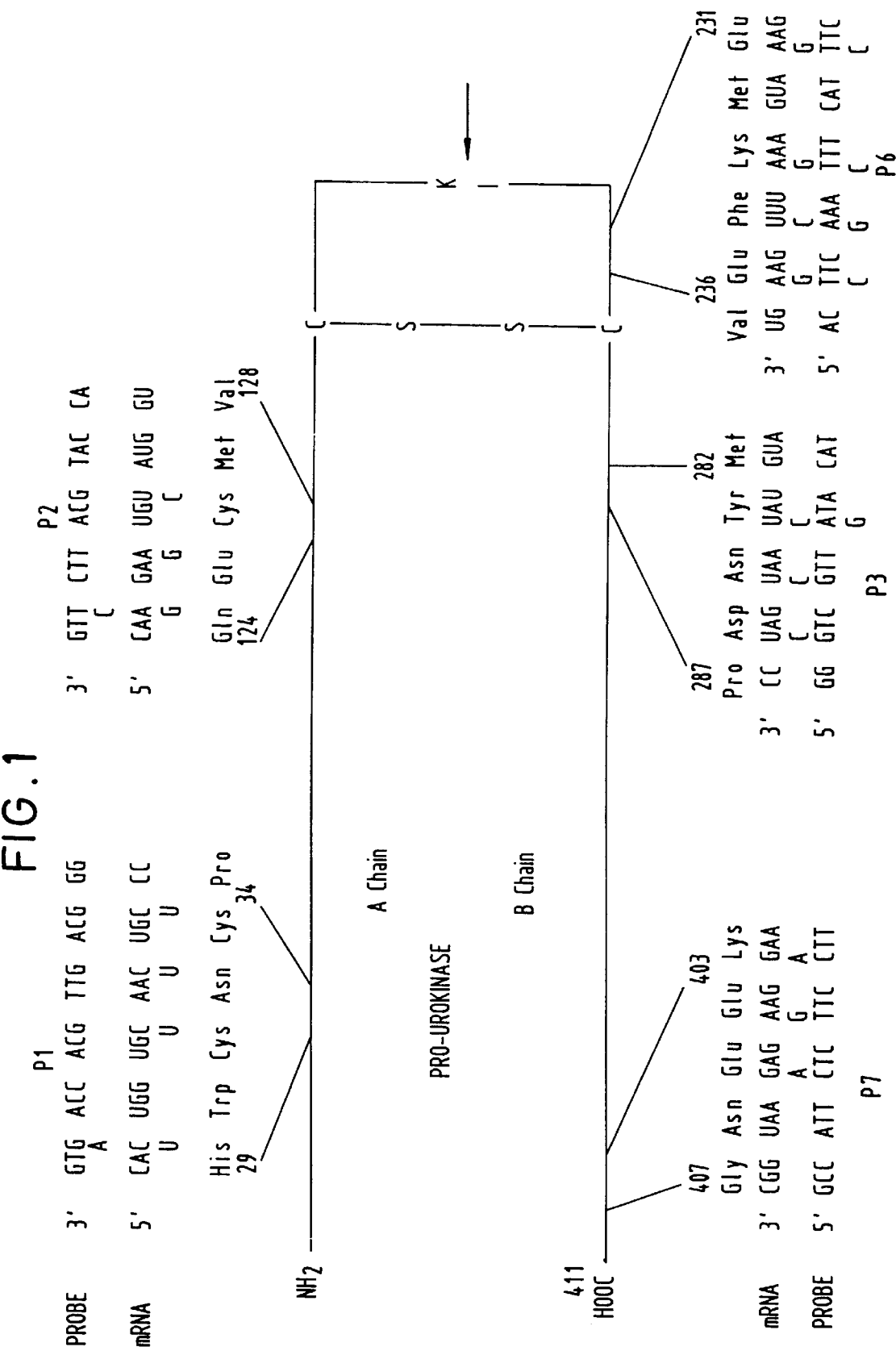

United States Patent [19]
Brandazza et al.

[11] Patent Number: 5,866,358
[45] Date of Patent: Feb. 2, 1999

[54] PRODUCTION OF HUMAN PROUROKINASE

[75] Inventors: Anna Brandazza, Rivolta d'Adda; Paolo Sarmientos, Milan; Gaetano Orsini, Gallarate, all of Italy

[73] Assignee: Vascular Laboratory Inc., Boston, Mass.

[21] Appl. No.: 536,556

[22] PCT Filed: Oct. 6, 1989

[86] PCT No.: PCT/EP89/01168

§ 371 Date: Jul. 11, 1990

§ 102(e) Date: Jul. 11, 1990

[87] PCT Pub. No.: WO90/04023

PCT Pub. Date: Apr. 19, 1990

[30] Foreign Application Priority Data

Oct. 11, 1988 [GB] United Kingdom .................. 8823833

[51] Int. Cl.[6] ............... C12N 1/21; C12N 9/72; C12P 21/02
[52] U.S. Cl. ......... 435/69.1; 435/71.1; 435/215; 435/320.1; 536/24.1
[58] Field of Search ................ 435/216, 252.3, 435/252.33, 320.1, 69.1, 71.1, 215; 536/27, 24.1; 935/6, 9, 14, 29, 41, 45, 46, 73

[56] References Cited

FOREIGN PATENT DOCUMENTS 0210279 2/1987 European Pat. Off. .
0236209 9/1987 European Pat. Off. .

OTHER PUBLICATIONS

Lewin, Genes (1985), John Wiley and Sons, pp. 163, 692.
Hibino et al., Agric. Biol. Chem. 52(2):329–336 (1988).
Kane et al., Tibtech, vol. 6 : 95–101 (1988).
Sutiphong et al, Mol. Biol. Med. (1987) 4, 307–322.
Devlin et al, Gene, 65 (1988) 13–22.
Gorski et al, Cell, vol. 43, 461–469, Dec. 1985 (Part 1).
Surek et al, Appl. Microbiol. Biotechnol. (1991) 34:488–494.
Proteine 90, May 24–25, 1990, Abstract, G. Nitti, et al., "Renaturation and Purification of Recombinant Pro–Urokinase Expressed in E. Col".
Convegno Annuale Della Societa Italiana Di Biochimica, Oct. 25–26, 1990, Abstract, G. Orsini, et al., "Production of Recombinant Prourokinase from *Escherichia coli* Inclusion Bodies".
Eur. J. Biochem., vol. 195, pp. 691–697, 1991, G. Orsini, et al., "Efficient Renaturation and Fibrinolytic Properties of Prourokinase and a Deletion Mutant Expressed in *Escherichia coli* as Inclusion Bodies".
Biotechnology, vol. 3, No. 10, Oct. 1985, W.E. Holmes et al.: "Cloning and expression of the gene for pro–urokinase in *Escherichia coli*", pp. 923–929.
Febs Letters, vol. 185, No. 2, Jun. 1985, Elsevier Science Publishers B.V.R. Renhof et al.: "Synthesis and functional activity of translation initiation regions in mRNA", pp. 277–281.
Nucleic Acids Research, vol. 11, No. 14, 1983, IRL Press, E. Remaut et al.: "Inducible high level synthesis of mature human fibroblast interferon in *Escherichia coli*", pp. 4677–4688.

*Primary Examiner*—Johnny F. Railey, II
*Attorney, Agent, or Firm*—Oblon, Spivak, McClelland, Maier & Neustadt, P.C.

[57] ABSTRACT

A method is provided for producing non-glycosylated single chain prourokinase (proUK). The method comprises cultivating bacterial strains of *E. coli* which have been transformed with plasmids carrying the cDNA sequence coding for proUK.

6 Claims, 9 Drawing Sheets

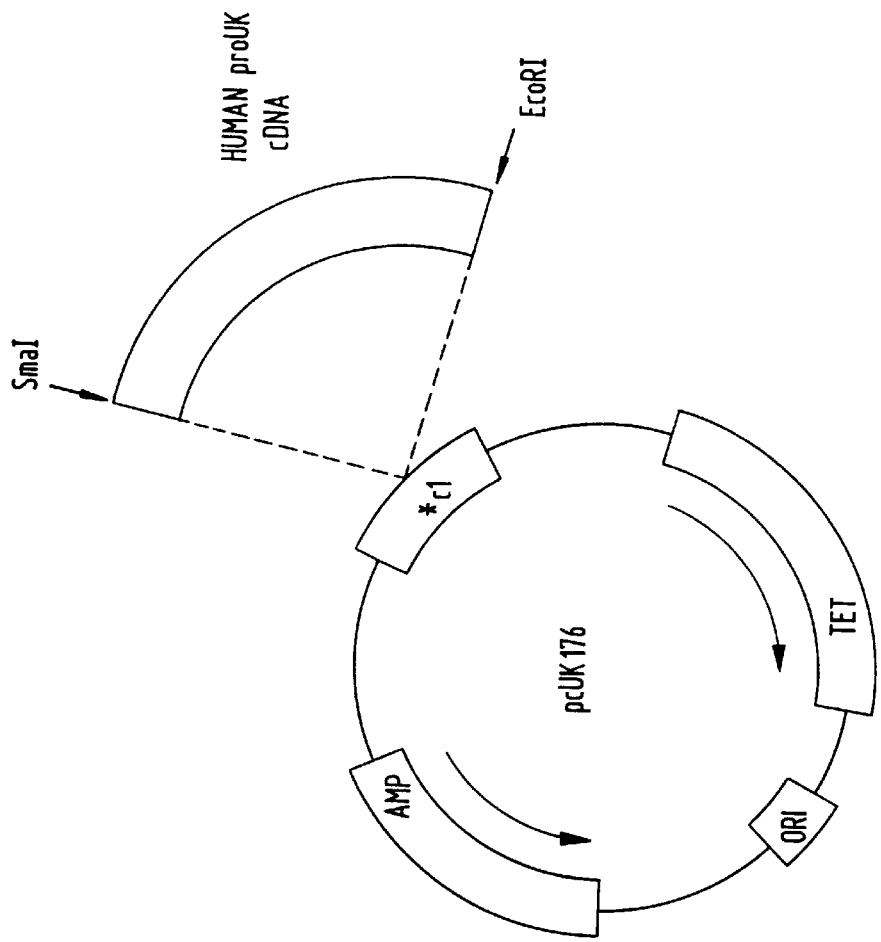
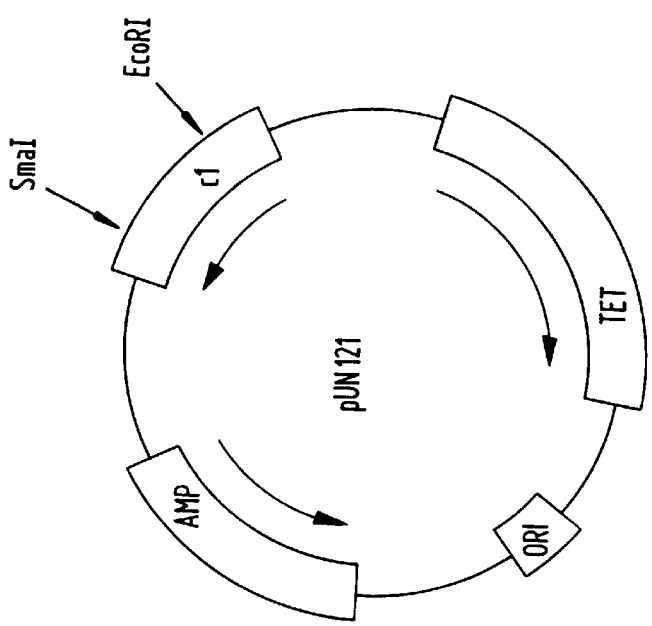
FIG. 3B
FIG. 3A

FIG. 4A

```
1 SmaI                                                    50
CCCGGGCTCCGGGCTGCGGTCTCCTGCCGCAGCCACCGAGCCGCCGTCTAGCGCCCCGACCTC
```

```
                                                      100
GCCACC ATG AGA GCC CTG CTG GCG CGC CTG CTT CTC TGC GTC CTG GTC
       Met Arg Ala Leu Leu Ala Arg Leu Leu Leu Cys Val Leu Val

150    TaqI
GTG AGC GAC TCC AAA GGC AGC AAT GAA CTT CAT CAA GTT CCA TGC AAC
Val Ser Asp Ser Lys Gly Ser Asn Glu Leu His Gln Val Pro Ser Asn

200
TGT GAC TGT CTA AAT GGA GGA ACA TGT GTG TCC AAC AAG TAC TTC TCC
Cys Asp Cys Leu Asn Gly Gly Thr Cys Val Ser Asn Lys Tyr Phe Ser

250
AAC AAT CAC TGG TGC AAC TGC CCA AAG AAA TTC GGA GGG CAG CAC TGT
Asn Ile His Trp Cys Asn Cys Pro Lys Lys Phe Gly Gly Gln His Cys

300
GAA ATA GAT AAG TCA AAA ACC TGC TAT GAG GGG AAT GGT CAC TTT TAC
Glu Ile Asp Lys Ser Lys Thr Cys Tyr Glu Gly Asn Gly His Phe Tyr

NcoI                              350
CGA GGA AAG GCC AGC ACT GAC ACC ATG GGC CGG CCC TGC CTG CCC TGG
Arg Gly Lys Ala Ser Thr Asp Thr Met Gly Arg Pro Cys Leu Pro Trp

BglII
AAC TCT GCC ACT GTC CTT CAG CAA ACG TAC CAT GCC CAC AGA TCT GAT
Asn Ser Ala Thr Val Leu Gln Gln Thr Tyr His Ala His Arg Ser Asp

400
GCT CTT CAG CTG GGC CTG GGG AAA CAT AAT TAC TGC AGG AAC CCA GAC
Ala Leu Gln Leu Gly Leu Gly Lys His Asn Tyr Cys Arg Asn Pro Asp

450
AAC CGG AGG CGA CCC TGG TGC TAT GTG CAG GTG GGC CTA AAG CCG CTT
Asn Arg Arg Arg Pro Trp Cys Tyr Val Gln Val Gly Leu Lys Pro Leu

500
GTC CAA GAG TGC ATG GTG CAT GAC TGC GCA GAT GGA AAA AAG CCC TCC
Val Gln Glu Cys Met Val His Asp Cys Ala Asp Gly Lys Lys Pro Ser

550
TCT CCT CCA GAA GAA TTA AAA TTT CAG TGT GGC CAA AAG ACT CTG AGG
Ser Pro Pro Glu Glu Leu Lys Phe Gln Cys Gly Gln Lys Thr Leu Arg

600
CCC CGC TTT AAG ATT ATT GGG GGA GAA TTC ACC ACC ATC GAG AAC CAG
Pro Arg Phe Lys Ile Ile Gly Gly Glu Phe Thr Thr Ile Glu Asn Gln

650
CCC TGG TTT GCG GCC ATC TAC AGG AGG CAC CGG GGG GGC TCT GTC ACC
Pro Trp Phe Ala Ala Ile Tyr Arg Arg His Arg Gly Gly Ser Val Thr
```

FIG. 4B

```
             700
TAC GTG TGT GGA GGC AGC CTC ATC AGC CCT TGC TGG GTG ATC AGC GCC
Tyr Val Cys Gly Gly Ser Leu Ile Ser Pro Cys Trp Val Ile Ser Ala
             750
ACA CAC TGC TTC ATT GAT TAC CCA AAG AAG GAG GAC TAC ATC GTC TAC
Thr His Cys Phe Ile Asp Tyr Pro Lys Lys Glu Asp Tyr Ile Val Tyr
             800
CTG GGT CGC TCA AGG CTT AAC TCC AAC ACG CAA GGG GAG ATG AAG TTT
Leu Gly Arg Ser Arg Leu Asn Ser Asn Thr Gln Gly Glu Met Lys Phe
             850
GAG GTG GAA AAC CTC ATC CTA CAC AAG GAC TAC AGC GCT GAC ACG CTT
Glu Val Glu Asn Leu Ile Leu His Lys Asp Tyr Ser Ala Asp Thr Leu
             900
GCT CAC CAC AAC GAC ATT GCC TTG CTG AAG ATC CGT TCC AAG GAG GGC
Ala His His Asn Asp Ile Ala Leu Leu Lys Ile Arg Ser Lys Glu Gly
             950
AGG TGT GCG CAG CCA TCC CGG ACT ATA CAG ACC ATC TGC CTG CCC TCG
Arg Cys Ala Gln Pro Ser Arg Thr Ile Gln Thr Ile Cys Leu Pro Ser
             1000
ATG TAT AAC GAT CCC CAG TTT GGC ACA AGC TGT GAG ATC ACT GGC TTT
Met Tyr Asn Asp Pro Gln Phe Gly Thr Ser Cys Glu Ile Thr Gly Phe
             1050
GGA AAA GAG AAT TCT ACC GAC TAT CTC TAT CCG GAG CAG CTG AAA ATG
Gly Lys Glu Asn Ser Thr Asp Tyr Leu Tyr Pro Glu Gln Leu Lys Met
             1100
ACT GTT GTG AAG CTG ATT TCC CAC CGG GAG TGT CAG CAG CCC CAC TAC
Thr Val Val Lys Leu Ile Ser His Arg Glu Cys Gln Gln Pro His Tyr
             1150
TAC GGC TCT GAA GTC ACC ACC AAA ATG CTA TGT GCT GCT GAC CCA CAA
Tyr Gly Ser Glu Val Thr Thr Lys Met Leu Cys Ala Ala Asp Pro Gln
             1200
TGG AAA ACA GAT TCC TGC CAG GGA GAC TCA GGG GGA CCC CTC GTC TGT
Trp Lys Thr Asp Ser Cys Gln Gly Asp Ser Gly Gly Pro Leu Val Cys
             1250
TCC CTC CAA GGC CGC ATG ACT TTG ACT GGA ATT GTG AGC TGG GGC CGT
Ser Leu Gln Gly Arg Met Thr Leu Thr Gly Ile Val Ser Trp Gly Arg
             1300
GGA TGT GCC CTG AAG GAC AAG CCA GGC GTC TAC ACG AGA GTC TCA CAC
Gly Cys Ala Leu Lys Asp Lys Pro Gly Val Tyr Thr Arg Val Ser His
        BamHI                                              1350
TTC TTA CCC TGG ATC CGC AGT CAC ACC AAG GAA GAG AAT GGC CTG GCC
Phe Leu Pro Trp Ile Arg Ser His Thr Lys Glu Glu Asn Gly Leu Ala
```

FIG. 4C

```
                                              1400
CTC TGA  GGGTCCCCAGGGAGGAAACGGGCACCACCCGCTTTCTTGCTGGTTGTCATTTTT
Leu end

1450
GCAGTAGAGTCATCTCCATCAGCTGTAAGAAGAGACTGGGAAGATAGGCTCTGCACAGATGGA

1500
TTTGCCTGTGCCACCCACCAGGGTGAACGACAATAGCTTTACCCTCAGGCATAGGCCTGGGTG 1550                                          1600
CTGGCTGCCCAGACCCCTCTGGCCAGGATGGAGGGGTGGTCCTGACTCAACATGTTACTGACC

1650
AGCAACTTGTCTTTTTCTGGACTGAAGCCTGCAGGAGTTAAAAAGGGCAGGGCATCTCCTGTG

1700                 NcoI
CATGGGTGAAGGGAGAGCCAGCTCCCCCGACGGTGGGCATTTGTGAGGCCATGGTTGAGAAA

1750
TGAATAATTTCCCAATTAGGAAGTGTAACAGCTGAGGTCTCTTGAGGGAGCTTAGCCAATGTG
1800                                              1850
GGAGCAGCGGTTTGGGGGAGCAGAGACACTAACGACTTCAGGGCAGGGCTCTGATATTCCATG

1900
AATGTATCAGGAAATATATATGTGTGTGTATGTTTGCACACTTGTGTGTGGGCTGTGAGTGTA

1950
AGTGTGAGTAAGAGCTGGTGTCTGATTGTTAAGTCTAAATATTTCCTTAAACTGTGTGGACTG 2000                                              2050
TGATGCCACACAGAGTGGTCTTTCTGGAGAGGTTATAGGTCACTCCTGGGGCCTCTTGGGTCC

2100
CCCACGTGACAGTGCCTGGGAATGTATTATTCTGCAGCATGACCTGTGACCAGCACTGTCTCA

2150
GTTTCACTTTCACATAGATGTCCCTTTCTTGGCCAGTTATCCCTTCCTTTTAGCCTAGTTCAT

2200
CCAATCCTCACTGGGTGGGGTGAGGACCACTCCTTACACTGAATATTTATATTTCACTATTTT

2250                                           EcoRI
TATTTATATTTTTGTAATTTTAAATAAAAGTGATCAATAAAATGTGATTTTTCTG(A)nGAATT
C
```

PRODUCTION OF HUMAN PROUROKINASE

This application is the national stage application of PCT/EP89/01168, filed Oct. 6, 1989.

The present invention relates to a recombinant DNA method of producing non-glycosylated single-chain prourokinase (hereinafter referred to as proUK). More particularly, it relates to a method of producing non-glycosylated proUK which comprises recovering mRNA from an established cell line, preparing cDNA based on said mRNA, inserting the cDNA into a vector, introducing the resulting plasmid into a bacterial cell to thereby produce a transformant and recovering non-glycosylated proUK from said bacterial cell. The invention concerns also certain expression plasmids employed in the above method.

INTRODUCTION

The increasing knowledge of the molecular interactions that regulate physiological fibrinolysis has lead to important implications in the understanding of the mechanisms that dissolve blood clots, and in the development of new thrombolytic agents.

In the human fibrinolytic system a proenzyme, plasminogen, can be activated to the active enzyme, plasmin, by several types of plasminogen activators (Collen, D. and Lijnen, H. R., CRC Critical Reviews in oncology/hematology, 4, n. 3,p. 249, 1986; Verstraete, M. and Collen, D.: Blood, 67, n. 6,p. 1529, 1986). Plasmin is the major protease responsible for the degradation of the fibrin component of a blood clot (Rakoczi, I., Wiman, B. and Collen, D.: Biochim. Biophys. Acta, 540, p. 295, 1978; Robbins, K. C. Summaria, L., Hsieh, B.; and Shah, R. S.: J. Biol. Chem. 242, p. 2333, 1967; Wiman, B.; Eur. J. Biochem, 76, p. 129, 1977).

However, plasmin can also exert its proteolytic effect on several plasma proteins among which the components of the coagulation pathway fibrinogen, factor V and VIII (Collen, D. and Lijnen, H. R., CRC Critical Reviews in oncology/hematology, 4, n. 3,p. 249, 1986; Verstraete, M. and Collen, D.: Blood, 67, n. 6,p. 1529, 1986; Wiman, B., Lijnen, H. R. and Collen, D.; Biochim, Biophys. Acta, 579, p. 142, 1979).

Activation of plasminogen may occur at the systemic level, leading to circulating plasmin that is rapidly neutralized by alfa2-antiplasmin and thus not available for fibrinolysis (Collen, D. and Lijnen, H. R., CRC Critical Reviews in oncology/hematology, 4, n. 3,p. 249, 1986; Verstraete, M. and Collen, D.: Blood, 67, n. 6,p. 1529, 1986).

When the alfa2-antiplasmin level is markedly reduced, plasmin is less rapidly neutralized and can exert its proteolytic effects not only on fibrin, but also on the blood coagulation proteins as described previously.

Excessive lowering in the plasma concentrations of fibrinogen, factor V and VIII, together with the inhibitory effects exerted by some of the fibrinogen degradation products on the hemostatic process, on platelet aggregation and on fibrin polymerisation lead to hemostatic deficiency and subsequently to high bleeding risk (Latallo, Z. S. and Lopaciuk, S.; Thrombos. Diath. Haemouh., 56, p. 253, 1973; Totty, W. G., Gilula, L. A., Mc. Clennman, M. Ahmed, P., and Sherman, L. Radiology, 143, p. 59, 1982). On the other hand, activation of plasminogen may occur at the fibrin level (fibrin-bound plasminogen activation) leading to fibrin-bound plasmin (Collen, D. and Lijnen, H. R., CRC Critical Reviews in oncology/hematology, 4, n. 3,p. 249, 1986; Verstraete, M. and Collen, D.: Blood, 67, n. 6,p. 1529, 1986) which is, instead, not affected by alfa2-antiplasmin and cannot induce systemic fibrinogenolysis.

Urokinase and streptokinase, the most commonly used plasminogen activators in conventional thrombolytic therapy in man, have no specific activity for fibrin. Both compounds activate relatively indiscriminately either circulating or fibrin-bound plasminogen (Zamarron, C., Lijnen, H. R., Van Hoef, B., and Collen, D., Thromb. Haemostas. 52, p. 19, 1984; Samama, M., and Kher, A. Sem. Hop. Paris. 61, n. 20. p. 1423, 1985). Therefore, the systemic haemostatic breakdown often encountered during treatment with streptokinase and urokinase and, consequently, the elevated bleeding risk have often hampered the widespread clinical use of these thrombolytic agents, despite their demonstrated clinical efficacy (Samama, M., and Kher, A. Sem. Hop. Paris, 61, n. 20. p. 1423, 1985; Maizel, A. S., and Bookstein, J. J.: Cardiovasc. Intervent. Radiol., 9, p. 236, 1986; Bell, W. R. Thromb. Haemostas., 35, p. 57, 1976; Acar, J., Vahanian, A., Michel, P. L., Slama, M., Cormier, B. and Roger, V., Seminars in Thromb. and Haemost., 13, n. 2, p. 186, 1987; Gruppo Italiano per lo studio della Streptochinase nell'infarto miocardico (GISSI); Lancet, 1, p. 397, 1986).

On the contrary, tissue-type plasminogen activator (t-PA) (Hoylaerts, M., Ryken, D. C., Lijnen, H. R. and Collen, D. J. Biol. Chem., 257, n. 6, p. 2912, 1982), and more recently prourokinase (pro-UK) (Husain, S. S., and Gurewich, V., Arch. Biochem. Biophys. 220 p. 31, 1983), both natural proteins, were shown to be weak activators of the circulating plasminogen and, conversely, strong activators of the fibrin-bound plasminogen, without either systemic haemostatic breakdown or consumption of alfa2-antiplasmin and plasminogen, thus their clinical use may cause lesser bleeding risk.

The fibrin-specific thrombolytic activity of t-PA has been explained by its ability to bind fibrin through specific lysine binding sites, located in the triple-disulfide-bonded "kringle domains" of the molecule.

Consequently, fibrin-bound plasminogen could be activated without significant haemostatic breakdown (Collen, D., and Lijnen, H. R.: Haemostasis; 16, n. 3, p. 25, 1986). On the other hand, proUK (also denominated single chain urokinase type plasminogen activator, scu-PA) does not bind to fibrin, however it displays fibrin-specific thrombolytic activity without systemic hemostatic consumption (Pannell, R. and Gurewich, V., Blood, 67, p. 1215, 1986; Gurewich V., and Pannell, R.; Seminars in Thromb. and Haemost., 13, n. 2, p. 146, 1987; Lijnen, H. R., Zamarron, C., Blaber, M., Winbler, M. E., and Collen, D., J. Biol. Chem. 261, p. 1253, 1986).

Recombinant t-PA was submitted to multicenter clinical trials in patients with acute myocardial infarctions and was shown to be significantly more effective than streptokinase in the recanalization of obstructed coronary arteries (The European Cooperative Study Group for Recombinant Tissue-type Plasminogen Activator; Lancet, 1 p. 842, 1985; Sheehan, F. H. Braunwald, E., Canner, P., Doodge, H. T., Gore, J., Van Natta P., Passamani, E. R. Williams, D. O., Zaret, B.: Circulation, 75, 4,p. 817, 1987).

Prourokinase is at present in advanced clinical trials and is thought to be, at least, as effective as t-PA in terms of thrombolytic activity and safety (Van de Werf, F., Nobuhara, M., and Collen, D.: Annals of Internal Medecine, 104, p. 345, 1986; Van de Werf, F., Vanhaecke, J., De Geest, H., Verstraete, M., and Collen, D.: Circulation, 74, n. 5, p. 1066, 1986)

BACKGROUND OF THE INVENTION

Urokinase-type plasminogen activators (u-PAs) are found in at least three different forms in human urine, plasma and conditioned culture medium from a variety of cell lines. The first form to be characterized as u-PA consisted of a fibrinolytically active polypeptide of 410 amino acids, with an apparent moelcular weight of 54000 daltons, containing two disulfide-linked chains (Gunzler, W. A., Steffens, G. J., Oetting, F., Kim, SM. A. Frankus, E., and Flohé, L.: Hoppe—Seyler's Z. Physiol. Chem. 363, p. 1155, 1982).

The A-chain or light chain contains 157 amino acids and one triple disulfide-bonded "kringle" structure. This chain also contains a receptor binding domain for normal and neoplastic cells (monocytes, monocyte-like cells and A 431 epidermoid cells). The B chain or heavy chain (30000 daltons) consists of 253 amino acids and contains the catalytic domain.

This molecular form of u-PA is generally termed urokinase (UK), two chain urokinase (TC-UK) or high molecular weight urokinase (HMW-UK)(Gunzler, W. A., Steffens, G. J., Oetting, F., Buze, G., and Flohé, L.: Hoppe-Seyler's Z. Phisiol. Chem. 363, p. 133, 1982). The second form of u-PA has a molecular weight of 33000 daltons and results from proteolytic degradation of the HMW form by either plasmin or trypsin. It is called low molecular weight urokinase (LMW-UK). Protein sequence determinations have revealed that LMW-UK is identical to HMW-UK except for the absence of the NH2-terminal 135 amino acids that are specifically removed by the action of plasmin or trypsin (Steffens, G. J., Gunzler, W. A. Oetting, F., Frankus, E., and Flohé, L., Hoppe-Seyler's Z. Phisiol. Chem., 363, p. 1043, 1982). Native prourokinase (proUK) is a single chain (54000 daltons) form of urokinase and is also termed single chain urokinase type plasminogen activator (scu-PA). As stated before, proUK displays a fibrin-specific thrombolytic activity and is therefore a better thrombolytic agent compared to the presently used high or low molecular weight urokinases.

In order to produce prourokinase, the authors of the present invention have developed a recombinant DNA procedure which allows the preparation of large amounts of the proUK polypeptidic chain.

Several methods have been described in the scientific and patent literature for the production of proUK (Holmes, W. E., Pennica, D., Blaber, M., Rey, M. W., Gunzler, W. A., Steffens, G. J. and Heynecker, H. L.; Biotechnology, 3 , p. 923, 1985; European Patent Application 0092182). However, the method described within the text of the present invention exploits parameters known to be important for the expression of heterologous proteins in E. coli, but whose combination has never been applied before to the production of recombinant proUK.

The main parameters, whose combination contributes to the establishment of a recombinant strain of E. coli, able to produce proUK, and which represents the object of the present invention, are the E. coli promoter Ptrp, the Shine-Dalgarno sequence MS-2 from the phage MS-2, and E. coli strains of the type B as hosts for the expression of the human proUK gene (see below).

Such combination is crucial. Substitution of one of these parameters with an alternative expression signal may not yield as much proUK.

Accordingly, object of the present invention is a method for the preparation of non glycosilated pro-UK, characterized in that non-glycosilated pro-UK is expressed under the control of the E. coli promoter Ptrp and the Shine-Dalgarno sequence MS-2 by E. coli B.

DESCRIPTION OF THE PRODUCTION PROCEDURE

The present invention relates to the construction, by genetic engineering techniques, of strains of E. coli able to express the human proUK gene at high levels. Consequently, these recombinant strains are able to synthesize large amounts of the proUK polypeptidic chain.

In order to isolate said recombinant strains of the bacterium E. coli, it is necessary to go through a number of steps including:

the isolation of the human cDNA gene coding for the desired proUK the insertion of said gene in an appropriate expression plasmid the transformation of selected strain of E. coli with the engineered plasmid and the cultivation of the transformants in appropriate conditions.

1) Cloning of the human cDNA gene coding for proUK

To obtain the cDNA clone coding for human prourokinase, the authors have utilized the proteins sequence data published in the literature (Gunzler, W. A., Steffens, G. J., Oetting, F., Kim, SM. A., Frankus. E., and Flohé, L.: Hoppe—Seyler's Z. Physiol. Chem., 363, p. 1155, 1982; Gunzler, W. A., Steffens, G. J., Oetting, F., Buze, G., and Flohé, L.: Hoppe-Seyler's Z. Phisiol. Chem. 363, p. 133, 1982; Steffens, G. J., Gunzler, W. A., Oetting, F., Frankus, E., and Flohé, L., Hoppe-Seyler's Z. Phisiol. Chem., 363, p. 1043, 1982).

Accordingly, specific probes have been prepared and an appropriate cDNA library has been screened.

Oligonucleotides coding for selected peptides of single-chain urokinase-type plasminogen activator (pro-UK) were chemically synthesized (Caruthers, M. H., Gassen, H. G. and Lang, J. A. (eds) Verlag-chimie, Weinheim, Deefield Beach, Basel, p. 71, 1982) to serve as specific probes to monitor enrichment of proUK mRNA and to select for clones containing prourokinase cDNA from an enriched cDNA library. The oligomers were 14 to 17 mer in length, and each one was synthetized either as unique sequence (named p7) or in pools containing two (named p1, p2, p3) or 16 (named p6) oligonucleotides as indicated in FIG. 1. The oligomers were tested for specificity to proUK by northern hybridization. For this analysis polyA-containing RNA was extracted from the HEp-3 epidermoid carcinoma (Miskin, R., Haemostasis (Switzerland), 11, No. suppl 1, p. 63, 1982). For each oligomer the temperature of the washing following the hybridization reaction was adjusted so as to be 2 to 5 degree C below the minimal melting temperature, as calculated according to Suggs et al. for hybridization to southern blots (Suggs, S. V., Hirose, T., Miyake, T., Kawashima, E. G., Johnson M. Y., Itakura, K. and Wallach, R. B., Developmental Biology Using Purified Genes; Brown D. D. and Fox, C. F. (eds) Academic Press, New York, p. 638, 1981). In this text the five proUK probes, shown in FIG. 1, reacted with one common major carcinoma mRNA band of about 2.3 kb, which is the size expected for proUK MRNA.

Cloning took place using enriched mRNA fractions from the HEp-3 epidermoid carcinoma. RNA preparations were extracted and enriched about 3 fold on two successive sucrose gradients. cDNA was synthesized according to published procedures (Efstratiadis, A., Kafatos, F. C., Maxam, A. M. and Maniatis, T. Cell, 7, p. 279, 1976; Buell, G. N., Wickens, M. P., Payvar, F. and Schimke, R. T. J. Biol. Chem. 253, p. 2471, 1978) using oligo-dT as a primer. Longer molecules were isolated using polyacrilamide gel electrophoresis followed by electro-elution of the appropriate gel fractions. The cDNA was then extracted using standard phenol/chloroform extraction followed by ethanol precipitation.

These cDNA molecules were first ligated to EcoRI linkers and then cloned into the phage λgt10 vector according to a modification of the technique of Davis (Maniatis, T., Fritsch, E. F., Sambrook, J.: Molecular cloning. A laboratory manual. Cold Spring Harbour Laboratory. Cold Spring Harbour, N.Y., 1982). By doing so, a library containing $2\times10^5$ pfu (plaque forming units) was constructed.

Half of the library was screened on duplicate filters, one filter with $^{32}$P-labelled probe p1, and the counterpart filter with a mixture of probes p3 and p6. A total of 36 positive clones were obtained, seven of which were positive in the duplicate filters, thus indicating cDNA inserts corresponding to a large portion of the proUK coding sequence.

Recombinant phages that hybridized with the 3 probes were plaques purified using probe p1, and further characterized by restriction mapping with EcoRI and by DNA sequencing. The fraction of the positive clones in the total cDNA library indicated that the frequency of prourokinase mRNA in the HEp-3 carcinoma is approximately 0.01%.

Figure 2:
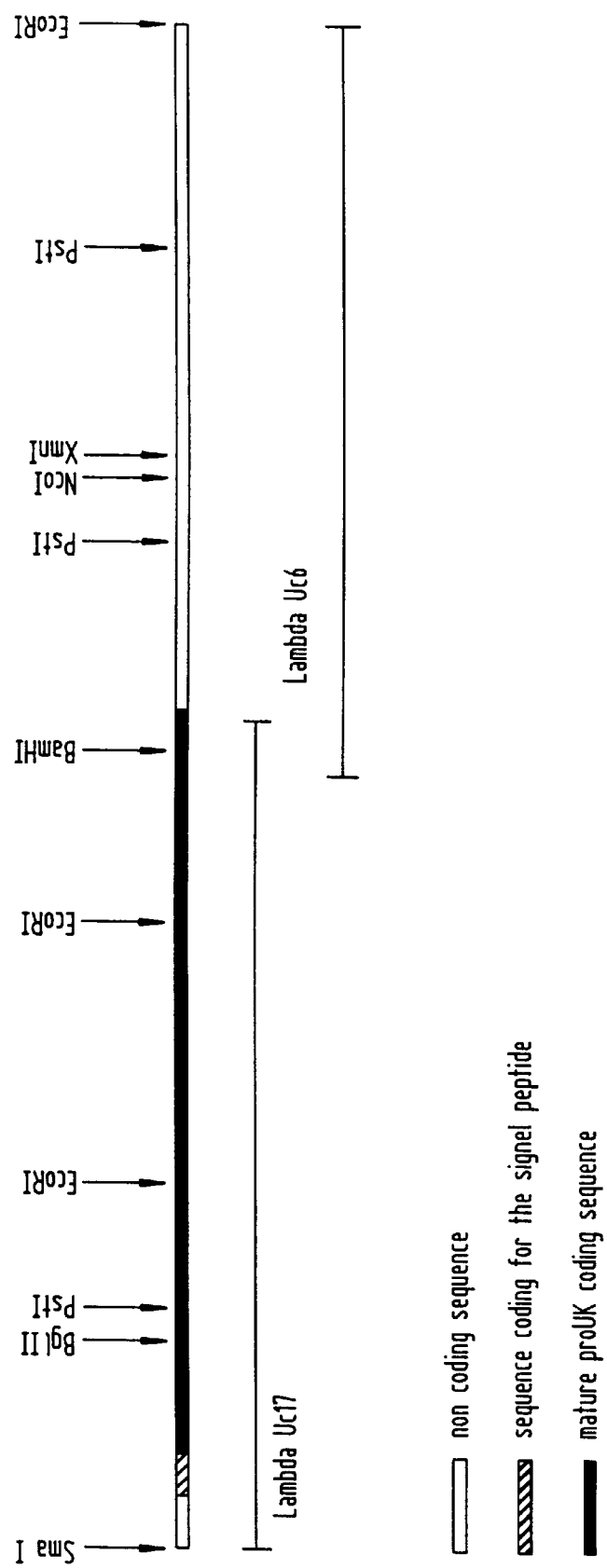
Figure 5A:
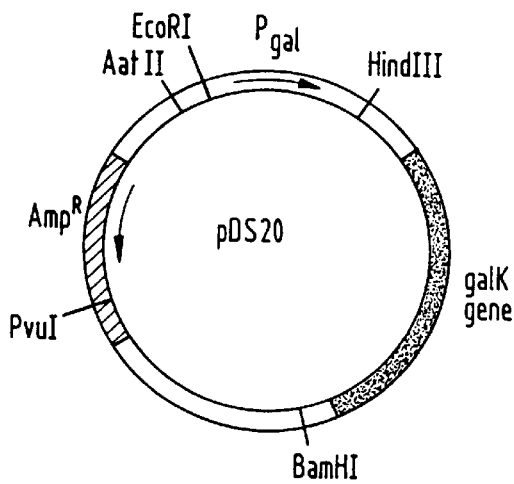
Figure 5B:
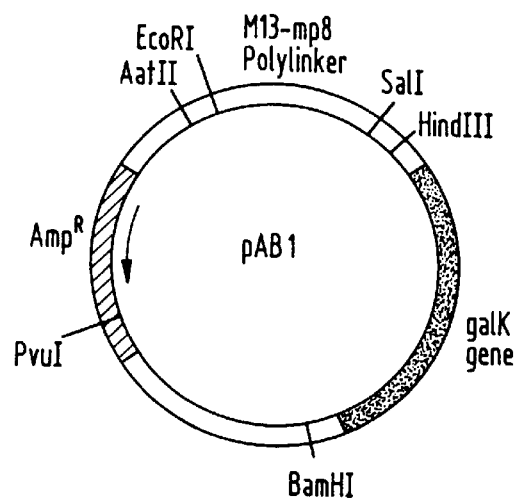
Figure 5C:
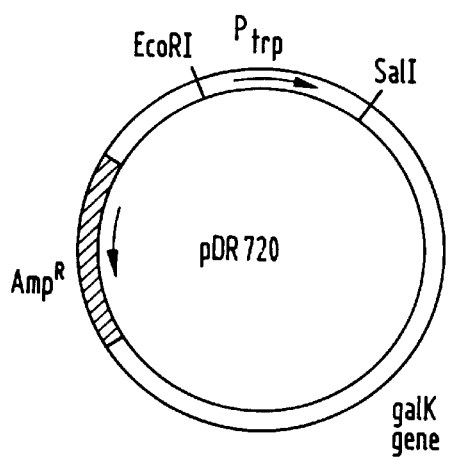
Figure 5D:
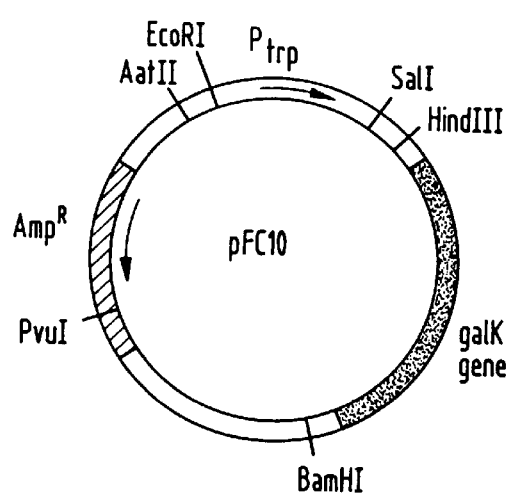

Sequence analysis of four proUK cDNA clones revealed that three of the clones had deletions or sequences not consistent with the amino acid sequence of the enzyme. Only one clone, λUc17, had a sequence with complete concordance with the known amino acid sequence. However, λUc17 did not include the entire 3' non-coding end of the mRNA and was missing 30 nucleotides of the coding sequence. A full length pre-prourokinase cDNA clone was constructed by ligation of a 1325 bp λUc17 SmaI-BamHI fragment, containing the 5' non-coding region and the majority of the coding sequence, with a BamHI-EcoRI fragment containing the remaining missing 3' region from another clone λUc6 (FIG. 2).

This construct was ligated into the SmaI-EcoRI site of the plasmid vector pUN121 (Nilsson B., Uhlen M., Josephson S., Gatenbeck S. and Philipson L., Nucleic Acid Research 11, p. 8019, 1983), eliminating, thus, most of the cI gene, and given the name pcUK176 (FIG. 3).

The DNA sequence of the complete cDNA clone is depicted in FIG. 4. It consists of 2296 nucleotides, including 69 non-coding nucleotides at the 5' end, 1296 coding nucleotides, and 931 non-coding nucleotides at the 3' end, followed by a poly(A) tail of more than 80 residues.

Figure 7:
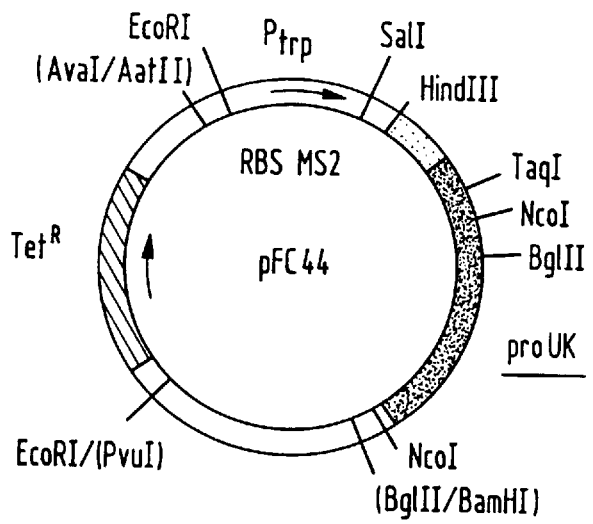

"Shine-Dalgarno" sequence MS-2, respectively. The plasmid pFC44 is shown in FIG. 7.

In order to obtain pFC44, several intermediate plasmids were constructed. Starting with pDS20 (FIG. 5) (Duester, G., Helfard, R. M. and Holmes, W. M.: Cell 30, p. 855, 1982), we have first replaced the EcoRI-HindIII fragment coding for the galactose operon promoter Pgal with the EcoRI-HindIII polylinker sequence from the M13 mp8 vector (Vieira, J. and Messing, I. Gene, 19, p. 259, 1982), obtaining a new plasmid, named pAB1 (FIG. 5).

The promoter Ptrp has been obtained from the plasmid pDR720 (bought from Pharmacia) as an EcoRI-SalI restriction fragment. This fragment has been inserted in the polylinker region of pAB1 between the EcoRI and the SalI site. By doing so, we have obtained a new plasmid, named pFC10 (FIG. 5).

pFC10 can be considred as the base vector into which we have inserted the proUK gene as well as the "Shine-Dalgarno" sequence from the phage MS-2.

To achieve expression of mature prourokinase, it is necessary to fuse the proUK coding sequence, from the first codon of the mature protein to the initiator triplet ATG. This fusion must then be preceded by the "Shine-Dalgarno" sequence.

The ribosome binding site (RBS) from the bacterial phage MS-2 was known and its nucleotide sequence had already been published (Fiers, W., Contreras, R., Duerinck, F., Haegeman, G., Iserentant, D., Merregaert, J., Min Jou, W., Molemans, F., Raeymaekers, A., Van den Berghe, A., Volckaert, G. and Ysebaert, M. Nature, 260, p. 500, 1976).

It is thought to be a strong signal for an efficient translation of the mRNA. Therefore, we have chosen this region as translation signal for the production of proUK. In order to obtain the correct nucleotide fusion with the proUK gene, we have synthesized a double strand DNA region of the MS-2 RBS directly joined to the beginning of the proUK gene. A TaqI site is present on the 25th nucleotide of the mature proUK sequence. We have taken advantage of this site and isolated, by chemical synthesis, the following DNA sequence:

```
                HindIII                                                    MetSer
5'-AGCTTTAATAGACGCCGGCCATTCAAACATGAGGATTACCCATGAGCA

3'-AATTATCTGCGGCCGGTAAGTTTGTACTCCTAATGGGTACTCGT

TaqI
           ATGAACTTCATCAAGTTCCAT-3'

TACTTGAAGTAGTTCAAGGTAGC-5'
```

The coding sequence starts with 60 bp coding for 20 amino acids comprising the "pre-prourokinase" (Heyneker, H. L., Holmes, W. E. and Vehar, G. A. (1983). European Patent Application Publ. No. 0092182), and is followed by the sequence coding for the entire prourokinase protein, which is in complete concordance with the amino acid sequence.

The complete fragment has been checked by sequence and restriction analysis. The sequence coding for mature prourokinase has been inserted into the expression vector used for production.

2) Construction of the proUK expression plasmid

The original full length cDNA, present in pcUK176, was used to construct a prourokinase expression plasmid, named pFC44, in which the proUK gene is under the transcriptional and the translational control of the promoter Ptrp and of the which is flanked upstream by an HindIII site and down stream by a TaqI site. The initiator codon ATG is shown in bold face. The sequence coding for the beginning of the mature proUK sequence is underlined.

The synthetic fragment has been used in a ligation reaction with the two following restriction fragments:
- the TaqI-BglII fragment from pcUK176 (FIG. 3), which carries the proUK sequence from nucleotide 155 to nucleotide 392 (see FIG. 4);
- the large BamHI-HindIII fragment from pFC10 (FIG. 5), which carries the antibiotic resistance to ampicillin as well as the promoter Ptrp.

Figure 6A:
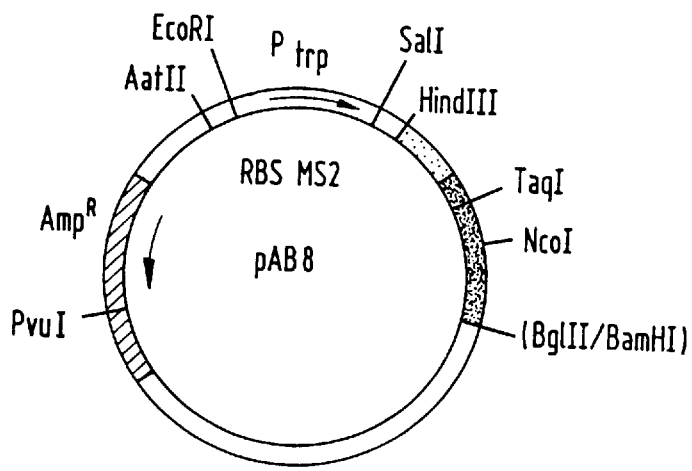
Figure 6B:
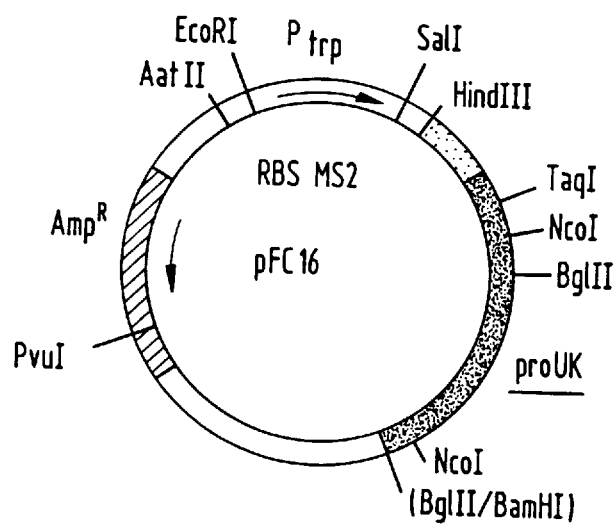
Figure 6C:
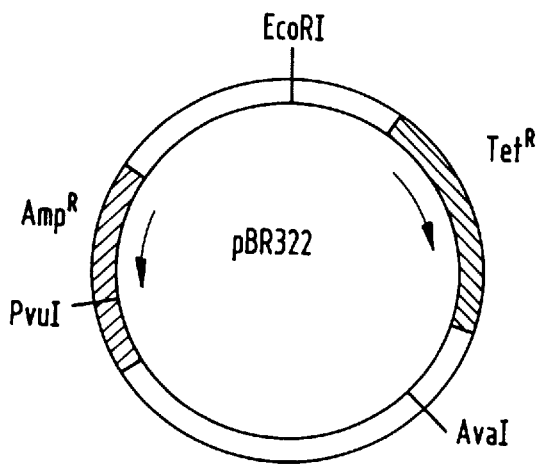

Through this construction, we have isolated a new plasmid, named pAB8, whose schematic map is shown in FIG. 6. In this plasmid, the promoter Ptrp and the MS-2 RBS are fused to the first 260 nucleotides of the mature proUK gene (corresponding to nucleotides 131–391 in FIG. 4). In addition, pAB8 has a unique NcoI site into which we have inserted the rest of the proUK sequence through a NcoI—NcoI restriction fragment from pcUK176. This ligation has caused the duplication of an NcoI-BglII fragment downstream of the proUK gene in the non-coding region. However, this duplication does not affect plasmid stability. Through this construction signals can now direct the synthesis of the complete proUK sequence (see FIG. 6).

All the plasmids, described so far, were selected in the E. coli K-12 host strain C-600 galK (ATCC 33955), on the basis of ampicillin resistance. Indeed, they carry the gene coding for β-lactamase, the enzyme responsible for the degradation of the antibiotic ampicillin in the culture medium. Early experiments have shown that pFC16 could be successfully inserted in E. coli type B strains and cause high level production of recombinant proUK.

However, to comply with international guidelines for the production of recombinant DNA-derived products, we have modified pFC16 to create a new tetracycline-resistant plasmid able to express the proUK gene at high levels. In particular, from the well-known plasmid pBR322 (Maniatis, T., Fritsch, E. F. Sambrook, J.: Molecular cloning. A laboratory manual. Cold Spring Harbour Laboratory. Cold Spring Harbour, N.Y. 1982) (FIG. 6), we have isolated a EcoRI-AvaI fragment where the sticky ends were filled in using the klenow fragment of DNA polymerase I (Perbal, B., A Wiley-Interscience Publication John Wiley and Sons, p. 231, 1984). This fragment was ligated to the larger AatII-PvuI fragment from pFC16, whose ends were made blunt by DNA polymerase I (Perbal, B., A Wiley-Interscience Publication John Wiley And Sons, p. 231, 1984). By doing so, we have replaced the amino terminal portion of the B-lactamase gene and its controlling sequence with the tetracycline-resistance gene. Following ligation the tetracycline resistance gene is in the same orientation as the proUK gene. Moreover, a new EcoRI site has been created at the junction between the PvuI and EcoRI sites, previously filled in. The new plasmid, pFC44 (see FIG. 7), is the final construction that has been used for the production of recombinant prourokinase.

Plasmid pFC44 (tetracycline-resistant) and pFC16 (ampicillin resistant) are one of the objects of the present invention. The expression signals, present in these two plasmids, namely the promoter Ptrp and the Shine-Dalgarno sequence "MS-2", have already been described in the literature for the expression of heterologous proteins (Remaut E., Stranssens P. and Fiers W. Nucl. Acid. Res. 11, p. 4677, 1983). However, their combination has never been applied before to the expression of the proUK gene.

3) Transformation of E. coli type B strains

The second main object of the present invention is the use of E. coli strains of the type B for the expression and production of prourokinase. Indeed, the authors of the present invention have found that insertion of plasmids pFC16 or pFC44 in type B strain of the bacterium E. coli brings to high level productions of the proUK polypeptidic chain. Interestingly, insertion of plasmids pFC16 or pFC44 in other strains of E. coli (type K-12, type C, type W, etc) does not yield as much proUK. Consequently, the host strain type seems to be crucial for the successful production of proUK. Several type B strains of E. coli are available and can be used for successful expression of the proUK gene. Prefered strains are: ATCC 12407, ATCC 11303, NCTC 10537. Below is an example of transformation of strain NCTC 10537 with plasmid pFC44 and subsequent cultivation of the transformant.

Figure 8:
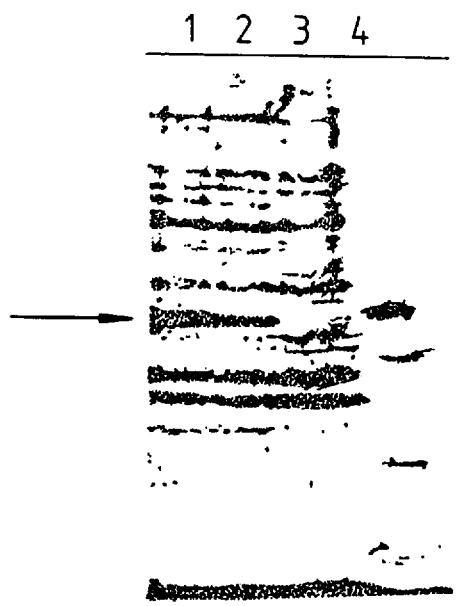

Competent cells of strain NCTC 10537 were prepared using the calcium chloride procedure of Mandel and Higa (Mandel, M. and Higa, A. J. Mol. Biol. 53, p. 154, 1970). Approximately 200 μl of a preparation of these cells at $1\times10^9$ cells per milliliter were transformed with 2 μl of plasmid DNA (approximate concentration 5 μg/ml). Transformants were selected on plates of L-agar containing 12.5 μg/ml tetracycline. Two small colonies were streaked with wooden tooth picks (each as three streaks about 1 cm long) onto L-agar containing the same antibiotic. After 12 hours incubation at 37° C., portions of the streaks were tested for human prourokinase production by inoculation onto 10 ml of LB medium (containing tetracycline at a concentration of 2.5 μg/ml) and incubated overnight at 37° C. The following day the cultures were diluted 1:100 in M9 medium, containing the same concentration of tetracycline, and incubated for 6 hours at 37° C. Total cell proteins from 250 μl aliquots of culture (O.D.$_{550}$=1–1.5) were analysed by sodium dodecylsulfate polyacrylamide gel electrophoresis as described by Laemmli (Laemmli, U.K. Nature, 227, p. 680, 1970). A major protein band having a molecular weight corresponding to that of non-glycosilated human prourokinase (45000 daltons) was observed for the two independent samples (FIG. 8).

The set of streaks corresponding to colony no. 2 (clone 2) was chosen arbitrarily for further characterization and then selected as a proUK producing strain.

MATERIALS AND METHODS

Growth Media: The media used were prepared using recipes as described by Maniatis et al. (Maniatis, T., Fritsch, E. F. Sambrook, J.: Molecular cloning. A laboratory manual. Cold Spring Harbour Laboratory. Cold Spring Harbour, N.Y. 1982). LB Medium, LB agar and MacConkey agar were prepared using Difcobacto Products. M9 medium is comprised of the following components: $Na_2HPO_4$, 6 grams/l; $KH_2PO_4$, 3 g/l: NaCl, 0.5 g/l; $NH_4Cl$, 1 g/l. After sterilization of the above components by autoclaving (1 atm.; 120° C. for 20 min.), 1 ml of 1M $MgSO_4$, 0.1 ml of 1M $CaCl_2$, 16 ml of 25% Glucose, 20 ml of 0.5 mg/ml Thiamine (SIGMA) and 20 ml of 20% Casamino Acids (DIFCO) were added per litre. The above solution is sterilized by filtration.

Use of Restriction Endonucleases and Other Enzymes: Restriction endonucleases, T4 DNA Ligase and DNA Polymerase I (Klenow Fragment) were obtained from New England Biolabs and from Boehringer Mannheim and were used in conditions recomended by the manufacturer.

Preparation of Plasmid DNA: Plasmid DNA was prepared by a method involving dye-buoyant density centrifugation based on the procedure of Birnboim and Doly (Birnboim, H. C. and Doly. J., Nucleic Acid Res. 7, p. 1513, 1979).

DNA sequence analysis: Sequence data were obtained using the Amersham M13 sequencing kit according to the instruction of the manufacturer. Briefly, this technique, based on the Sanger method (Sanger, F., Science, 214, p. 1205, 1981) consists of subcloning various restriction fragments in convenient M13 vectors (the "mp family") which can be obtained in their single strand configuration. After annealing the single strand forms with "universal primers", it is possible to copy the DNA template with DNA polymerase I (klenow fragment). By copying the template in the presence of the four dideoxynucleotides it is possible to cause random terminations of the chain elongation. The truncated fragments are then separated on denaturing polyacrylamide gels and the electrophoretic profile is evidenced by autoradiography.

Oligonucleotides: Synthetic oliognucleotides, utilized in plasmid constructions and as primers in DNA sequencing, were synthesized using the Applied Biosystem (ABI) DNA synthesizer 380B according to the ABI manual.

Other procedures: Procedures for agarose and polyacrilamide gel electrophoresis of nucleic acids were as described by Maniatis et al. (Maniatis, T., Fritsch, E. F. Sambrook, J.: Molecular cloning. A laboratory manual. Cold Spring Harbour Laboratory. Cold Spring Harbour, N.Y., 1982). Proteins were separated by polyacrylamide gel electrophoresis as described by Laenmli (Laermili, U. K. Nature, 227, p. 680, 1970). DNA was extracted from agarose gels by electrophoresis into dialysis bags and was concentrated by ethanol precipitation.

LEGENDS TO FIGURES

FIG. 1: The nucleotide sequence of probes P1, P2, P3, P6 and P7, the complementary mRNA sequence and the proUK peptides coded by the probes are depicted.

FIG. 2: The size and location of restriction endonuclease cleavage products were estimated by electrophoresis and confirmed by DNA sequence analysis. The filled region indicates the coding sequence of the mature proUK protein, the cross-hatched region represents the "pre-pro" peptide coding sequence and the open regions indicate the 5' and the 3' non-translated sequences. The 5' end of the mRNA is to the left. The lines below the restriction map indicate the contribution of the two partial clones $\mu$Uc17 and $\mu$Uc6.

FIG. 3: The EcoRI-SmaI fragment carrying the cDNA clone has been inserted in pUN121 replacing most of the cI gene. Plasmid pcUK176 is still tetracycline and ampicillin resistant. *cI represents an inactivated cI protein.

FIG. 4: The complete cDNA sequence of clone pcUK176 is depicted with the corresponding translated amino acid sequence. Restriction sites which have been used for plasmid constructions are underlined. Two polyadenilation sites at position 2264 and 2277 and the Serine residue at position 1 of the mature proUK sequence are also underlined.

FIG. 5: In this figure four intermediate constructions are depicted. The starting plasmid, pDS20, carries the general background which, through the different intermediate plasmids, loses the promoter Pgal, the galK gene and the β-lactamase gene.

FIG. 6: Three additional intermediate constructions including plasmid pFC16 which expresses high level of proUK. For details, see the text.

FIG. 7: In pFC44 the mature proUK coding sequence is under control of the promoter Ptrp and of the "ribosome binding site" from the phage MS-2. The tetracycline gene has been inserted at the place of the β-lactamase gene. pFC44 is therefore ampicillin sensitive.

FIG. 8: The samples were prepared and analysed as described in the text and loaded on a 12.5% SDS-polyacrylamide gel (acryl to bisacrylamide ratio 40:1). Lanes 1 and 2 contain material derived from two cultures of strain NCTC 10537 transformed with pFC44. The position of the recombinant prourokinase protein is indicated by the arrow. Lane 3 shows material derived from the control host strain NCTC 10537. A molecular weight standard is shown in lane 4.

DISCUSSION AND CONCLUSIONS

The present invention relates to a recombinant DNA method for the production of non-glycosilated prourokinase. This method is based on the insertion of the human gene coding for proUK in bacterial strains of *E. coli* and the subsequent cultivation of said transformed strains.

The production of heterologous proteins in *E. coli* is a well studied field of modern biotechnology (Harris T. J. R. and Emtage J. S. Microbiological Sciences, 3, p. 28–31, 1986). Today the molecular biologists know of several expression signals such as promoters, Shine-Dalgarno sequences, terminators, etc. that can be used for the protein of choice. The promoter is responsible for the synthesis of messenger RNA while the Shine-Dalgarno sequence should guarantee an efficient translation of the mRNA in polypeptidic chain.

The combination, however, of these parameters is an important feature in the heterologous gene expression. For example, fusion of an efficient Shine-Dalgarno sequence to different promoter regions can lead to different expression levels. In addition, the length of the restriction fragments carrying the expression signals often affects the levels of production (McCarthy J. E. G., Sebald W., Gross G. and Lammers R.; Gene, 41, p. 201, 1986).

The choice of the host strain is also a critical step in the development of an efficient method of production. It is, in fact, known that insertion of the same expression plasmid in different strains can lead to very different expression efficiencies (Harris T. J. R. and Emtage J. S. Microbiological Sciences, 3, p. 28–31, 1986).

While the expression signals described in the present invention were already known in the scientific literature, their combination had never been exploited before for the specific expression of human prourokinase. More particularly, plasmids pFC16 and pFC44 carry the proUK gene under control of the *E. coli* promoter Ptrp and the phage Shine-Dalgarno sequence MS-2.

Consequently, the production method, disclosed within the text of the present invention, is based on expression plasmids essentially different from other expression plasmids previously described. These plasmids, pFC16 and pFC44, represent therefore one of the novelty aspects of the present invention and, as already said, are an object thereof.

In addition, the method here disclosed takes advantage of *E. coli* strains of the type B. The vast majority of the expression methods, described in the scientific literature, is based on strains of *E. coli* of the type K-12. Thus, the production of proUK in *E. coli* strains of the type B represents another novelty aspect of the present invention.

This second aspect is extremely important. The choice of the host organism can, in fact, affect the global production process at several steps.

For instance, fermentations at high biomass may dramatically be influenced by the type of host. The present inventors as well as other groups of researchers have consistently found that *E. coli* strains of the type B can be grown more easily than, e.g., K-12 strains. Insertion of the same expression plasmids, pFC16 or pFC44, in K-12 strains such as C600 generates recombinant strains, which cannot grow, in fermentators, as efficiently as the recombinant B strains. In other words, yields of recombinant non-glycosilated pro-UK are higher from B strains, when using the same expression plasmids.

Another important feature related to the choice of the host strain is the different nature of the bacterial contaminants during the pro-UK production process. Undesired contaminants, such as proteases, could severely affect yields of the recombinant product. Interestingly, in 1986, Winkler and Blaber (Winkler, M. E., Blaber, M.: Biochemistry, 25, n. 14, p. 4041, 1986) have described a pro-UK production process based on the K-12 strain 294 (ATCC 31446).

In this process, the authors had to take several precautions to avoid proteolytic digestion of pro-UK. According to the authors these proteolytic activity was due to bacterial proteases from the host strain.

In contrast the use of B strains according to the present invention yields cell extracts with much lower proteolytic activity. In particular, it has been found that pro-UK extracted from the K-12 strain C600 is contaminated by urokinase to a higher extent compared to pro-UK from B strains.

In conclusion, the authors of the present invention, believe that the higher yields of recombinant pro-UK observed with the here described procedure compared with the prior art, represent an unpredictable result and an improvement over the known procedures.

We claim:

1. A method for the preparation of non-glycosylated pro-UK, characterized in that non-glycosylated human pro-UK is expressed under the control of the *E. coli* promoter Ptrp and the Shine-Dalgarno sequence MS-2 by *E. coli* B wherein the sequence comprising the Shine-Dalgarno sequence MS-2, the ATG start codon and the beginning of the pro-UK gene, flanked upstream by a HindIII site and downstream by a TaqI site is as follows:

HindIII

5'-AGCTTTAATAGACGCCGGCCATTCAAACATGAGGATT

-continued
3'-AATTATCTGCGGCCGGTAAGTTTGTACTCCTAA

ACCCATGAGC

TGGGTACTCG

TaqI

AATGAACTTCATCAAGTTCCAT-3'

TTACTTGAAGTAGTTCAAGGTAGC-5' and said HindIII site is downstream of the promoter Ptrp.

2. A method according to claim 1 wherein the non-glycosylated single chain prourokinase has a molecular weight of about 45000 daltons.

3. The method according to claim 1, characterized in that the cDNA sequence for pro-UK is obtained from MRNA of HEp-3 epidermoid carcinoma cells.

4. The method according to claim 1, characterized in that the promoter Ptrp constitutes of an EcoRI-SalI restriction fragment obtained from the plasmid pDR-720.

5. Expression plasmid FC-16 according to FIG. 6.

6. Expression plasmid FC-44 according to FIG. 7.

* * * * *